United States Patent [19]

Ogawa

[11] Patent Number: 4,772,778
[45] Date of Patent: Sep. 20, 1988

[54] TEMPERATURE-CONTROLLED ELECTRIC DEVICE FOR HEATING TRANSFUSION FLUIDS

[76] Inventor: Genshiro Ogawa, 13-3, Aza-Nishikoken Oaza-Inuyama Inuyama-shi Aichi-ken, Japan

[21] Appl. No.: 29,602

[22] Filed: Mar. 24, 1987

[30] Foreign Application Priority Data

Jun. 16, 1986 [JP] Japan .................. 61-139472

[51] Int. Cl.$^4$ .......... H05B 1/02; A61F 7/00; B67D 5/62; F24H 1/12
[52] U.S. Cl. .................. 219/302; 165/46; 219/303; 219/305; 219/308; 219/328; 219/330
[58] Field of Search .................. 219/296–299, 219/301–309, 328–331; 604/113, 114; 165/46; 128/399

[56] References Cited

U.S. PATENT DOCUMENTS

| 3,485,245 | 12/1969 | Lahr et al. .................. 219/302 X |
| 4,167,663 | 9/1979 | Granzow et al. .................. 219/309 X |
| 4,293,762 | 10/1981 | Ogawa .................. 219/330 X |
| 4,309,592 | 1/1982 | Le Boeuf .................. 219/308 X |
| 4,473,739 | 9/1984 | Scheiwe et al. .................. 219/302 |
| 4,532,414 | 7/1985 | Shah et al. .................. 219/330 X |
| 4,680,445 | 7/1987 | Ogawa .................. 219/302 X |

FOREIGN PATENT DOCUMENTS 2350264  4/1974 Fed. Rep. of Germany ...... 219/302
1578015 10/1980 United Kingdom ................ 219/302

Primary Examiner—Anthony Bartis
Attorney, Agent, or Firm—Burns, Doane, Swecker & Mathis

[57] ABSTRACT

Device for heating transfusion fluids, such as blood and drugs in solution, prior to their intravenous drop-by-drop introduction to patients, which comprises a case having therein a heater and an electric circuit, a heating plate disposed in a front face of the case and having, on its surface, a groove following a winding course at its middle portion and adapted to receive therein a transfusion fluid conduit, and a lid for closing said case on the side of its front face. The heater is connected to the back side of the heating plate, so as to heat the heating plate. The electric circuit includes a fluid-temperature thermistor, a heater-temperature thermistor, and a heating-plate temperature thermistor. Electric input to the heater is controlled on the basis of the temperature determined by the fluid-temperature thermistor, so that the fluid through the conduit may have its predetermined temperature. The electric input to the heater is interrupted when the temperature of the heater-temperature thermistor or of the heating-plate temperature thermistor has increased beyond a certain predetermined value, thus preventing the fluid from being overheated even temporarily or partly.

5 Claims, 5 Drawing Sheets

TEMPERATURE-CONTROLLED ELECTRIC DEVICE FOR HEATING TRANSFUSION FLUIDS

BACKGROUND OF THE INVENTION

1. Field of the Invention

This invention relates to a device for heating transfusion fluids such as blood and drugs in solution prior to their intravenous drop-by-drop introduction to patients and, in particular, to a heating device with the above-mentioned function which is characterized in controlling the temperature of transfusion fluid to a suitable one which approximates the human body temperature, as well as in preventing the fluid from being heated beyond a certain predetermined temperature if the rate of flow of the fluid has considerably changed during drip transfusion.

2. Description of the Prior Art

Fluids for transfusion are generally stored at a temperature of 4 degree centigrade. In order to be able to safely inject the fluid into the veins of a patient, it is necessary to heat the fluid from the cold state up to the human body temperature or an approximate temperature, i.e., 37 degrees centigrade or so. There are two different manner of doing this: One is to heat the entire fluid quantity to be administrated, at one time, together with its container, and the other is to heat the fluid as it flows through a conduit connected to the fluid container. The former manner takes much time, and thus is not useful in case of emergency, while the latter manner makes it possible to heat a required amount of transfusion fluid when required. So, in most cases, the latter manner is followed.

U.S. Pat. No. 4,293,762 (issued on Oct. 6, 1981) discloses a device for heating a transfusion fluid flowing through an conduit connected to the fluid container which comprises a case having therein an electric circuit and a heater, a heating plate disposed in the front face of the case and having a groove with a winding portion, and a lid for closing the case. The electric circuit includes two thermistors. One of them measures the temperature of fluid flowing and heated through the conduit disposed in and through the groove, and operates the electric circuit to cause the heater to output intermittently for the purpose of giving a predetermined temperature to the fluid through the conduit. The other thermistor is connected to the heater for breaking the circuit if the heater has been heated beyond a predetermined temperature due to an extremely increased rate of flow of the fluid through the conduit.

However, this prior art has the following disadvantage. Usually the operational temperature of the above-second mentioned thermistor is set at a value higher than the temperature to which the fluid is to be heated (e.g., 63 degrees centigrade), so that the heater can be prevented from being heated beyond the operational temperature of the thermistor. Nevertheless it is not possible to protect the heating plate against becoming extremely hot. Then, in particular, in case of an appreciable reduction or increase of the rate of flow of the fluid, it may be overheated temporarily or partly, resulting in its coagulation or deterioration.

OBJECTS AND SUMMARY OF THE INVENTION

A primary object of the invention is to provide an improved device for heating transfusion fluids such as blood and drugs in solution, without coagulating or deteriorating them, prior to their intravenous introduction to patients.

Another object of the invention is to provide an electric circuit used for a device of the character described which functions to prevent a heating plate or a heater provided in the device from becoming hot beyond a predetermined temperature.

Still another object of the invention is to provide a device of the character described which is capable of protecting the fluid against overheat in case of an appreciable reduction or increase of the rate of flow of the fluid through the conduit.

The foregoing and other objects and features of the invention will become apparent from a detailed description of the preferred embodiment of the invention and from the claims. Also, upon reading this specification, various advantages of the invention will be apparent to those skilled in the art.

According to the invention, a transfusion fluid heating device is provided which includes a case with a front face and having therein a heater and an electric circuit, a heating plate disposed in said front face of said case and having a groove following a winding course at its middle portion and adapted to receive therein a transfusion fluid conduit, and a lid for closing said case on the side of said front face thereof. A heater is bonded to the back side of the heating plate. A thermistor is connected to the heater for measuring its temperature. Also, a thermistor is provided on an outlet side of the groove for measuring the fluid temperature. Moreover, a thermistor is connected to the heating plate for measuring its temperature. The electric circuit functions to control a thermal output of the heater, on the basis of the fluid temperature determined by the foregoing second-mentioned thermistor, so that the fluid through the conduit may have a predetermined temperature. On the other hand, if the first-mentioned thermistor (the heater-temperature thermistor) or the third-mentioned thermistor (the heating-plate temperature thermistor) has become hot beyond a predetermined temperature, the electric circuit interrupts an electric input to the heater.

DETAILED DESCRIPTION OF THE PREFERRED EMBODIMENT

Figure 1:
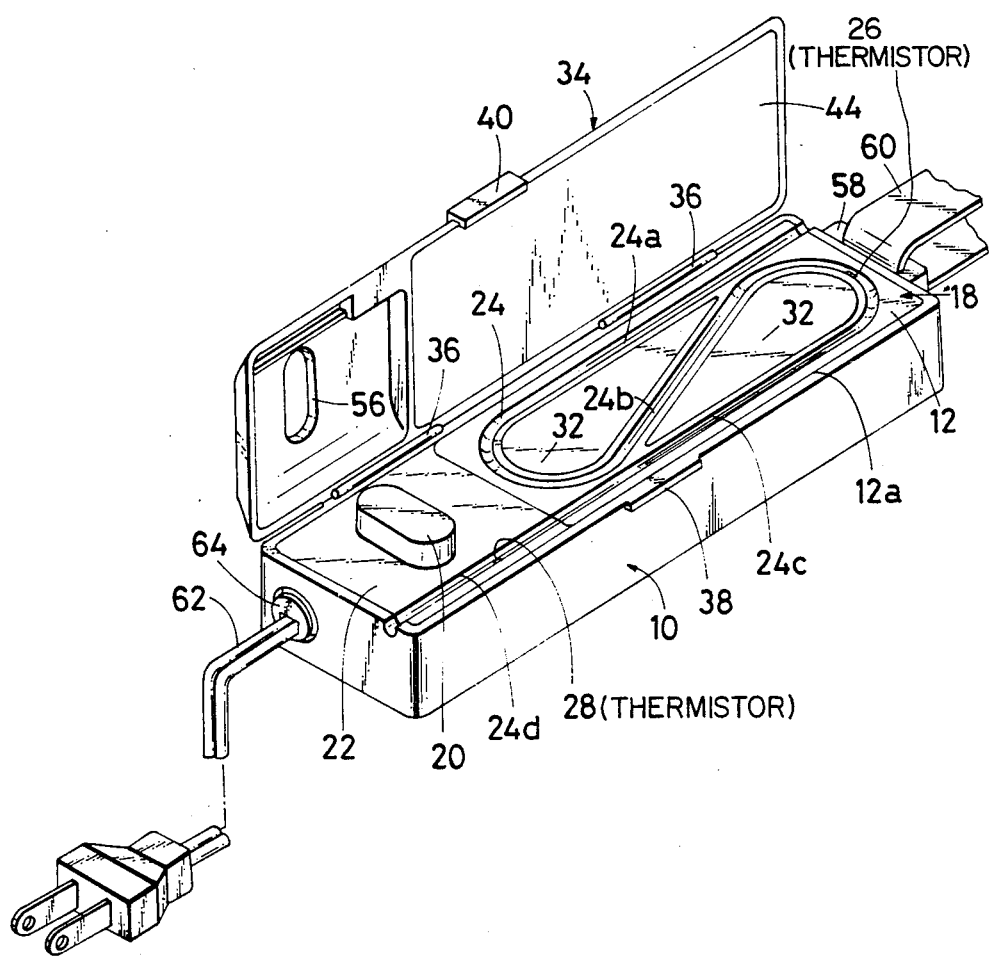
FIG. 1 is a perspective view of a transfusion fluid heating device according to the invention. In this view a lid of the device is opened.

Referring to the drawings, the most preferred embodiment of the invention will now be described in detail.

Figure 2:
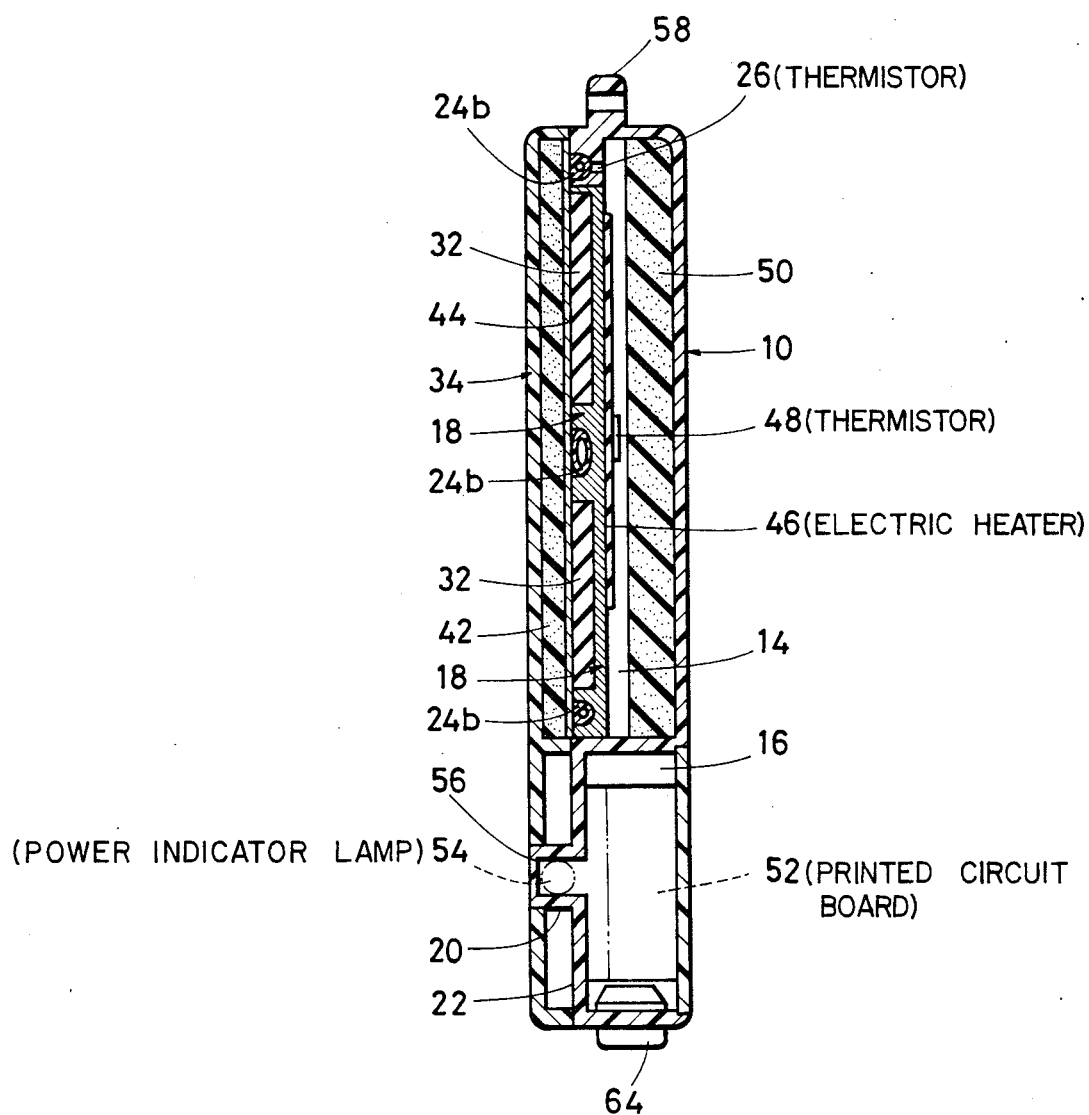
FIG. 2 is a cross section taken on the line II—II of FIG. 3.
Figure 3:
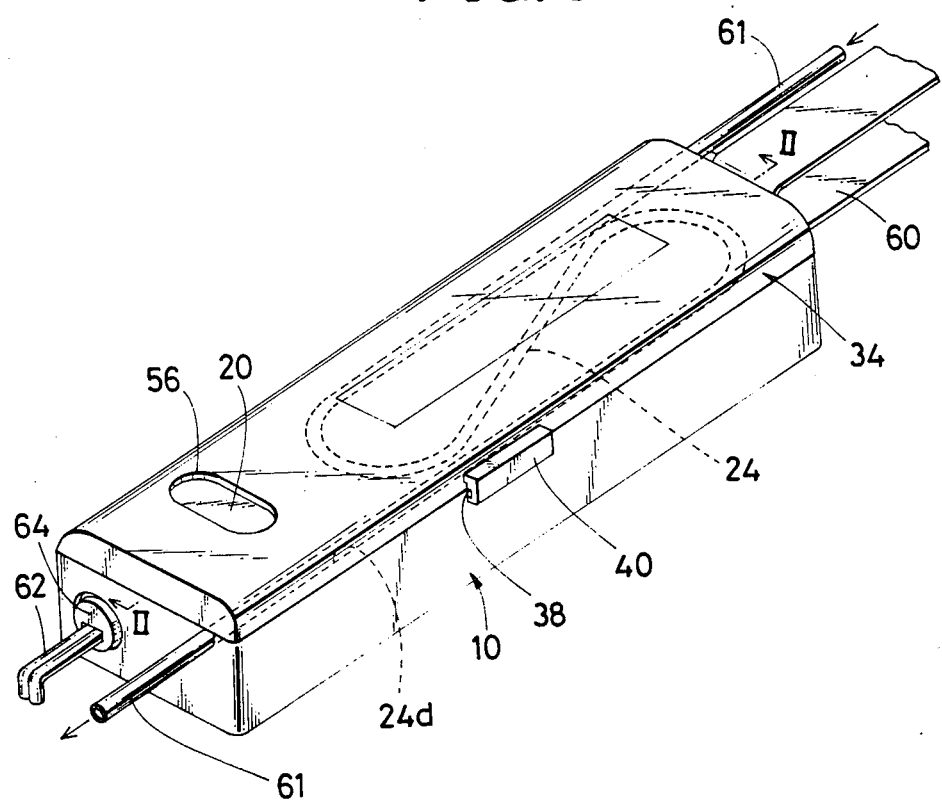
FIG. 3 is another perspective view of the heating device. In this view, a transfusion fluid conduit is disposed in and through the device and its lid is closed.
Figure 4:
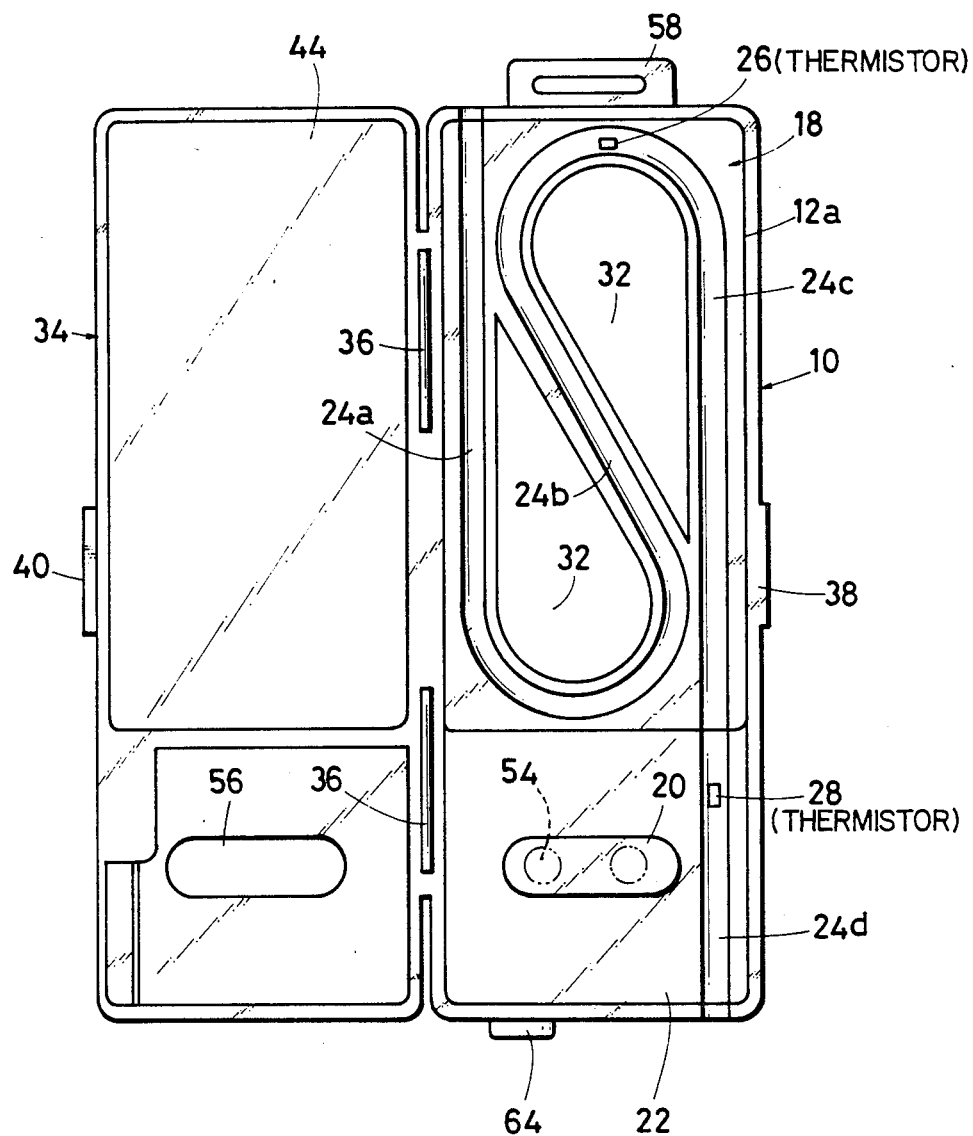
FIG. 4 is a plan view of the heating device with its lid being fully opened.

A device for heating transfusion fluids according to the invention includes a box-shaped case 10 having an inner front face 12 and a lid 34 connected to one side thereof by means of hinges 36. The inside of the case 10 is divided into a heater-housing chamber 14 and a circuit-elements chamber 16. The inner front face 12 of the case 10 has a heating plate 18 at its section 12a on the heater-housing chamber 14, and has a cover 22 at its section on the circuit-elements chamber 16. The cover 22 has a cavity 20 in which a power lamp 54 (FIG. 2) is disposed. The heating plate 18 is provided, on its surface, with a single continuous groove 24 having a U-shaped cross section and into which a conduit for transfusion fluid can be closely fitted. The groove 24 comprises a first straight portion 24a extending from a corner of the heating plate 18 along the length direction of the plate 18, a central S-shaped portion 24b, and a second straight portion 24c extending from the end of the central S-shaped portion along the length direction of the plate 18. The second straight portion 24c of the groove 24 communicates directly with another similar groove 24d for the transfusion fluid conduit formed on the surface of the cover 22. The central S-shaped portion 24b of the groove 24 has therein a thermistor 26 for measuring the temperature of the heating plate 18. The thermistor 26 is located near the end of the central portion 24b. Also, the groove 24d has therein a thermistor 28 for measuring the temperature of the fluid conduit. The portion of the surface of the heating plate 18 surrounded by a greater portion of the first straight portion 24a and a greater portion of the central S-shaped portion 24b, as well as that of the surface of the heating plate 18 surrounded by the remaining portion of the central portion 24b and a greater portion of the second straight portion 24c, are recessed to receive therein silicone rubber members 32. The lid 34 is provided, at one side thereof, with a hook 40 which is adapted to engage with a projection 38 provided on the opposite side to the hinges 36 for the lid 34, so as to hold the lid closed. A press plate 44 of aluminum is secured to the inside of the lid 34 through a heat-insulating material 42. As shown in FIGS. 2 and 3, the press plate 44 serves to press against a transfusion fluid conduit 61 in order to prevent it being removed from the groove 24, as well as to closely fit the conduit 61 onto the groove 24.

As shown in FIG. 2, the heating plate 18 on the heaterhousing chamber 14 is provided with a heater 46 having an electric heating element disposed in a rubber layer at the inner surface thereof. The heater 46 is bonded to the plate 18. A thermistor 48 is connected to the inner surface of the heater 46 for measuring its temperature. In the heater-housing chamber 14, a heat-insulating material 50 is fixed to the back wall of the chamber 14. Inside the circuit-elements 52 wired onto a printed circuit board. An opening 56 is made through the lid 34 in a position corresponding to that of the groove 20, which houses the power lamp 54, and when the lid 34 is closed, the groove 20 is exposed therefrom so that the power lamp 54 with its on or off condition may be directly seen from outside. On the top of the case 10 is connected a projection 58 having a central opening through which a band 60 passes to enable the case 10 and, hence, the entire heating device, to be suspended from a desired place. A bushing 64 is provided through the bottom of the case 10, and a power cord 62 passes through the bushing 64 to be connected to the printed circuit board.

Figure 5:
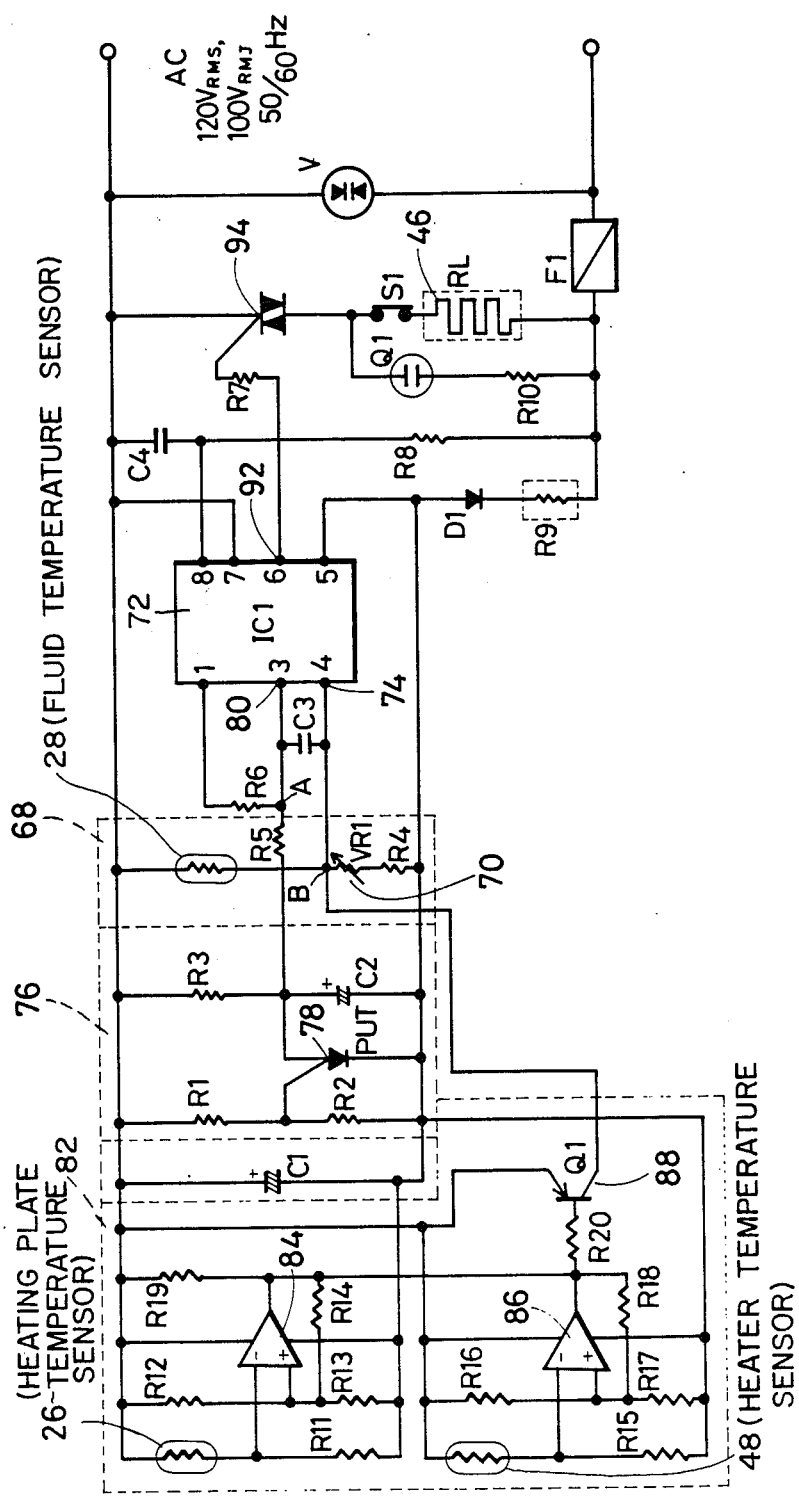
FIG. 5 is a diagram of an electric circuit used for the device.

Referring to FIG. 5, an electric circuit for controlling the temperature of the heater 46 will now be described. In FIG. 5, numeral 68 designates a circuit for measuring the temperature of a transfusion fluid which comprises a fluid-temperature thermistor 28 and a variable resistor 70. The output of this circuit 68 is coupled to a noninverting input terminal 74 of a zero-volt on/off control IC 72. Numeral 76 designates a triangular-wave generating circuit which is adapted to produce ramp outputs slowly, with a time constant of approximately 10 seconds as determined by a resistor R3 and a condenser C2 on the basis of the operation of PUT 78. The cycle period of the ramp output is considerably longer than that of the commercial power (50/60 Hz), and considerably shorter than the temperature constant of such means as heater 46, heating plate 18 or the like. The ramp output of the ramp generator 76 is coupled to an inverting input terminal 80 of the integrated circuit 72. Also, the integrated circuit 72 has a pulse-producing terminal 92 connected to a triac 94 through a resistor R7. The integrated circuit 72 causes the triac 94 to be ignited only when the voltage of the inverting input terminal 80 is higher than that of the noninverting input terminal 74. This ignition of the triac 94 is made at a voltage of around 0 V. The heater 46 is thus intermittently electrified and heated at intervals smaller than its time constant. The time of duration of this electrification is controlled by the temperature of the fluid-temperature thermistor 28.

Numeral 82 designates a heater-input stop circuit including a first operational amplifier 84 which is adapted to compare the voltage of the heating-plate temperature thermistor 26 with a predetermined voltage and a second operational amplifier 86 which is adapted to compare the voltage of the heater temperature thermistor 48 with a predetermined voltage. The output of each operational amplifier is coupled to a base of a transistor 88. The transistor 88 has a collector connected to the noninverting input terminal 74 of the integrated circuit 72, and also has an emitter connected to an electric circuit. Thus, when the transistor 88 is made conductive, the voltage of the noninverting input terminal 74 of the integrated circuit 72 is pulled up to the line voltage, so as not to allow the triac 94 to be ignited, irrespective of the temperature of the fluid-temperature thermistor 28.

Reference will now be made to the operation of the electric circuit with the above-mentioned construction. If and when the fluid flowing through the conduit disposed in the groove 24 has a low temperature, the fluid-temperature thermistor 28 of the fluid-temperature measurement circuit 68 has a large resistance, and thus has an output of low level. Then this output is applied to the noninverting input terminal 74, and is compared with the output of the ramp generator 76 applied to the inverting input terminal 80. If and while the output from the circuit 76 is higher than that from the circuit 68, the pulse output terminal 92 sends signals to the triac 94, so as to cause the heater 46 to be energized to produce heat. The heater 46 is thus enabled to raise the temperature of the fluid through the conduit. On the other hand, if the fluid has a temperature higher than necessary, the resistance of the thermistor 28 becomes smaller, and the output from the circuit 68 becomes higher and, thus, the time during which the output from the circuit 76 is higher than that from the circuit 68 becomes shorter. Therefore, the time duration of supply of signals from the pulse-producing terminal 92 to triac 94, and thus the time duration of the energizing of the heater 46, becomes shorter so that the temperature of the fluid is lowered.

In the heater-input stop circuit 82, if and when the temperature of the heating-plate thermistor 26 or of the heater-temperature thermistor 48 is lower than its predetermined temperature, the output levels of both first and second operational amplifiers 84 and 86 are high, and thus the transistor 88 is off. Then, if the temperature of the heating-plate thermistor 26 or of the heater-temperature thermistor 48 becomes higher than its predetermined temperature, the voltage of the inverting terminal of the amplifer 84 or 86 increases, and the output of the amplifier 84 or 86 is inverted to have a lower level. Then, current flows through the base of the transistor 88 to turn on the transistor 88, and the fluid-temperature thermistor 28 develops a short circuit, with the result that the level of output from the circuit 68 increases and becomes higher than the output voltage of the inverting input terminal 80 of the integrated circuit 72, thus interrupting the ignition of the triac 94. Therefore, the electrification of the heater 46 is discontinued, and the temperature of the heater 46 or of the heating plate becomes lowered to or below its predetermined temperature.

According to the invention, the energizing and, hence, heating of the heater 46 is controlled, as mentioned above, on the basis of the temperature of the fluid determined by the fluid-temperature measurement means. In particular, it should be noted that, since the electrification of the heater is interrupted when the heating plate or the heater has reached a certain predetermined temperature, the transfusion fluid through the conduit is prevented from being heated, even temporarily or partly, beyond a certain predetermined temperature. This advantage it is understood promotes an increase in the safety of operation of transfusion of blood or other fluid.

The present invention has been described in detail with reference to its most preferred embodiment. It is apparent that certain changes and modifications may be made without departing from the spirit and scope of the invention. It is intended all matters contained in the above description and in the accompanying drawings shall be interpreted only as illustrative and not in a limiting sense.

What is claimed is:

1. A transfusion fluid heating device which includes (a) a case with a front face and having therein an electrically energized heater and an electric circuit for controlling the energizing of said heater, (b) a heating plate disposed in said front face of said case and having, on its surface, a groove following a winding course at its middle portion and adapted to receive therein a transfusion fluid conduit, and (c) a lid for closing said case on the side of said front face thereof, and is characterized in that:

(A) said heater is bonded to the back side of said heating plate; and
   (B) said electric circuit includes (i) a means for determining the temperature of transfusion fluid heated by said heating plate, (ii) a means for determining the temperature of said heating plate, (iii) a means for determining the temperature of said heater, (iv) a means for controlling an electric input to said heater, in response to the fluid temperature determined by said fluid temperature determining means (i), so that the fluid has a predetermined temperature, and (v) a means for stopping an electrical input to said heater when one of the temperature of said heating plate determined by said heating plate temperature determining means (ii) and of said heater determined by said heater temperature determining means (iii) has increased beyond a certain predetermined value.

2. A device in accordance with claim 1 wherein said means (ii) for determining the temperature of said heating plate comprises a thermistor provided in said groove of said heating plate.

3. A device in accordance with claim 1 wherein said front face of said case is provided with a groove which directly communicates with said groove of said heating plate, and said means (i) for determining the temperature of transfusion fluid heated by said heating plate comprises a thermistor provided in said groove which directly communicates with said groove of said heating plate.

4. A device in accordance with claim 1 further including a means for suspending the device which comprises a projection connected onto the top of said case and having a central opening, and a band passing through this central opening.

5. A device in accordance with claim 1 wherein said lid has an inner member for pressing against the transfusion fluid conduit disposed in said groove of said heating plate, when said lid is closed, so as to closely fit the conduit on the above-mentioned groove and firmly hold it thereagainst, and heat-insulating materials are provided between said lid and said inner member thereof and between said inner member and said heating plate, respectively.

* * * * *